US010603016B2

United States Patent
Otomaru et al.

(10) Patent No.: US 10,603,016 B2
(45) Date of Patent: Mar. 31, 2020

(54) IMAGE PROCESSING APPARATUS, METHOD OF CONTROLLING THE SAME, AND NON-TRANSITORY COMPUTER-READABLE STORAGE MEDIUM

(71) Applicant: CANON KABUSHIKI KAISHA, Tokyo (JP)

(72) Inventors: Itaru Otomaru, Kawasaki (JP); Takaaki Endo, Urayasu (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 245 days.

(21) Appl. No.: 15/678,233

(22) Filed: Aug. 16, 2017

(65) Prior Publication Data

US 2018/0064422 A1 Mar. 8, 2018

(30) Foreign Application Priority Data

Sep. 7, 2016 (JP) .................................. 2016-174964

(51) Int. Cl.
*A61B 8/08* (2006.01)
*A61B 6/00* (2006.01)
(Continued)

(52) U.S. Cl.
CPC .......... *A61B 8/5246* (2013.01); *A61B 6/5247* (2013.01); *G06F 3/04845* (2013.01);
(Continued)

(58) Field of Classification Search
CPC ....... A61B 8/5246; A61B 6/5247; G06T 7/33; G06T 7/74; G06T 7/337;
(Continued)

(56) References Cited

U.S. PATENT DOCUMENTS 9,420,973 B1\* 8/2016 Konchitsky ............ A61B 5/684
9,588,666 B2 3/2017 Otomaru et al.
(Continued)

FOREIGN PATENT DOCUMENTS

JP 2015130972 A 7/2015
JP 2016021998 A 2/2016

OTHER PUBLICATIONS

Rueckert et al. "Nonrigid Registration Using Free-Form Deformations: Application to Breast MR Images.", IEEE Transactions on Medical Imaging. Aug. 1999:712-721. vol. 18, No. 8. Cited in Specification.

*Primary Examiner* — Bobbak Safaipour
(74) *Attorney, Agent, or Firm* — Rossi, Kimms & McDowell LLP

(57) ABSTRACT

An image processing apparatus obtains, in both a first image obtained by capturing an object and a predetermined space including the object, a corresponding feature part of the object, specifies a first point on the first image and a second point on the predetermined space, calculates a degree of matching between the first point and the second point, based on a positional relationship between the first point on the first image and the feature part of the object, and a positional relationship between the second point on the predetermined space and the feature part of the object on the predetermined space, and causes a display unit to display the calculated degree of matching.

30 Claims, 7 Drawing Sheets

US 10,603,016 B2
Page 2

(51) Int. Cl.
*G06T 7/33* (2017.01)
*G06F 3/0484* (2013.01)
*G06T 7/73* (2017.01)
*G06T 7/13* (2017.01)
*G06T 7/00* (2017.01)

(52) U.S. Cl.
CPC ............... *G06T 7/33* (2017.01); *G06T 7/337* (2017.01); *G06T 7/74* (2017.01); *G06T 7/0012* (2013.01); *G06T 7/13* (2017.01); *G06T 2207/10088* (2013.01); *G06T 2207/10136* (2013.01); *G06T 2207/20101* (2013.01)

(58) Field of Classification Search
CPC . G06T 2207/10136; G06T 2207/10088; G06T 7/0012; G06T 2207/20101; G06T 7/13; G06F 3/04845
See application file for complete search history.

(56) References Cited

U.S. PATENT DOCUMENTS

| | | | | |
|---|---|---|---|---|
| 10,028,711 | B2* | 7/2018 | Sakaguchi | A61B 6/504 |
| 10,157,465 | B2* | 12/2018 | Sugiyama | A61B 8/0825 |
| 10,297,024 | B2* | 5/2019 | Yang | G06T 7/11 |
| 2006/0274928 | A1* | 12/2006 | Collins | A61B 6/00 382/132 |
| 2008/0118138 | A1* | 5/2008 | Zingaretti | G06T 7/0012 382/132 |
| 2009/0154782 | A1* | 6/2009 | Zhang | G06T 3/0081 382/128 |
| 2011/0077523 | A1* | 3/2011 | Angott | A61B 5/0059 600/448 |
| 2011/0254942 | A1* | 10/2011 | Suzuki | G06K 9/00221 348/77 |
| 2012/0140989 | A1* | 6/2012 | Hori | G06T 7/136 382/106 |
| 2012/0253173 | A1* | 10/2012 | Endo | G06T 11/008 600/411 |
| 2014/0056502 | A1* | 2/2014 | Twellmann | G06T 7/0012 382/131 |
| 2014/0301648 | A1* | 10/2014 | Kato | G06T 7/001 382/199 |
| 2014/0348404 | A1* | 11/2014 | Jerebko | G06T 7/0012 382/131 |
| 2015/0178925 | A1* | 6/2015 | Jo | G06F 19/321 382/131 |
| 2015/0196282 | A1* | 7/2015 | Ishida | A61B 8/5261 600/443 |
| 2016/0155247 | A1* | 6/2016 | Robinson | A61B 8/4254 382/131 |
| 2016/0314587 | A1 | 10/2016 | Ishikawa et al. | |
| 2017/0039717 | A1* | 2/2017 | Otomaru | G06T 7/33 |
| 2017/0055844 | A1* | 3/2017 | Umezawa | A61B 5/744 |
| 2017/0212661 | A1* | 7/2017 | Ito | G06F 3/04815 |
| 2017/0301081 | A1* | 10/2017 | Yang | G06T 7/11 |
| 2018/0055458 | A1* | 3/2018 | Tsuda | A61B 5/7425 |
| 2018/0161012 | A1* | 6/2018 | Bang | A61B 6/4417 |

* cited by examiner

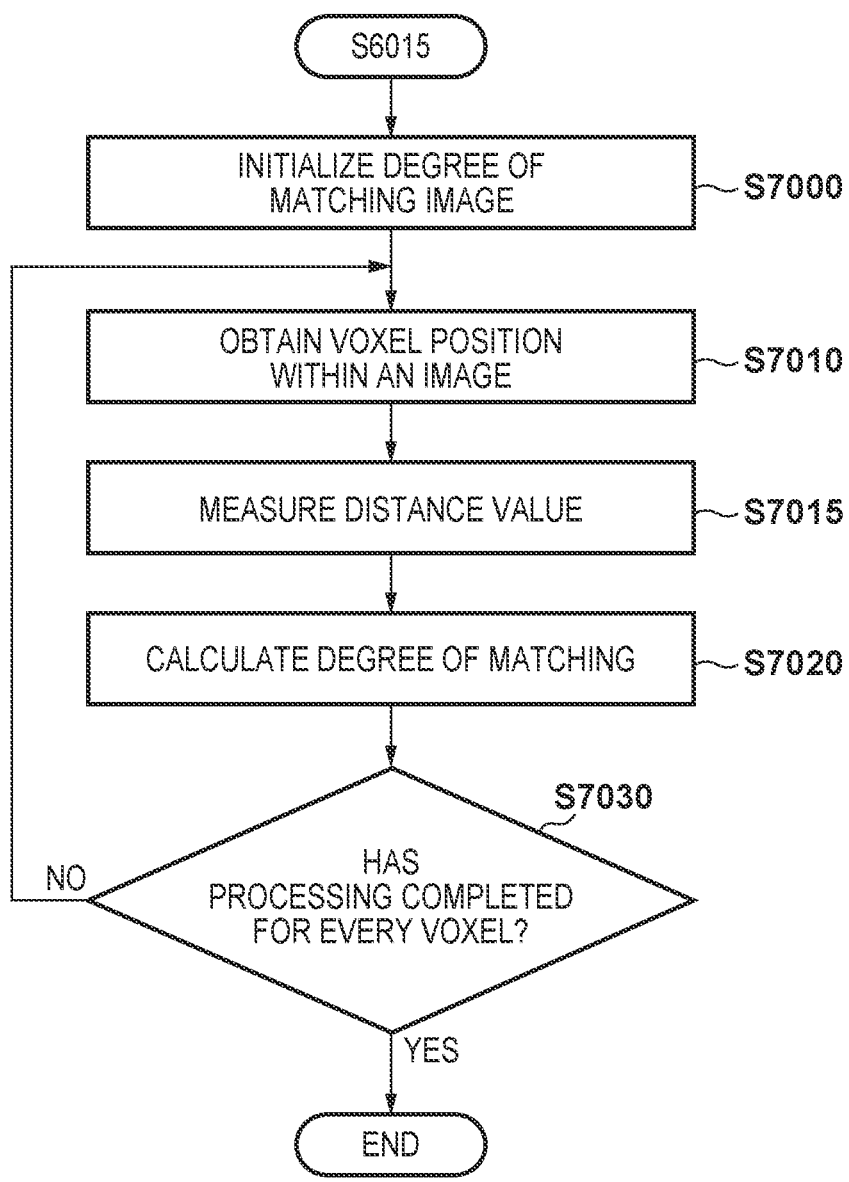

IMAGE PROCESSING APPARATUS, METHOD OF CONTROLLING THE SAME, AND NON-TRANSITORY COMPUTER-READABLE STORAGE MEDIUM

BACKGROUND OF THE INVENTION

Field of the Invention

The present invention relates to a technique of processing an image captured by various image capturing devices (modalities).

Description of the Related Art

In the field of medicine, in order to use medical images captured by a plurality of modalities or medical images captured at different dates, different postures, or by different capturing modes for a diagnosis, identification (association) of a point of interest on an object between respective medical images is important. For a point of interest, an automatic identification by image processing is possible, but difficulties sometimes exist for automatic identification due to modality differences, deformation of the object, or the like. For this reason, a doctor generally performs an identification operation by visual observation while viewing an image.

Also, for a similar purpose, registration and display of a plurality of images has been attempted. For example, a deformation registration technique for estimating a deformation of an object between images is disclosed in D. Rueckert, L. Sonoda, C. Hayes, D. Hill, M. Leach, and D. Hawkes, "Nonrigid registration using free-from deformations: application to breast MR images", IEEE med. imag., vol. 18 (8), pp. 712-721, 1999. Here, in order to realize higher precision registration, using corresponding points that the user identifies by a visual observation in a registration process is often performed.

Accordingly, a technique for supporting an operation of searching for and identifying a point of interest indicated on one image (hereinafter referred to as a reference image) from another image (hereinafter referred to as a target image) is being developed. For example, according to the technique of Japanese Patent Laid-Open No. 2016-21998, it is estimated whether or not points respectively inputted in relation to a reference image and a target image are correct as corresponding points, and this is presented to the user as an index of "a degree of matching". In the technique of Japanese Patent Laid-Open No. 2016-21998, in a case where many correctly associated points have already been obtained, a deviation amount from a displacement field calculated by using this group of points is used as a degree of matching.

However, the technique recited in Japanese Patent Laid-Open No. 2016-21998 has a problem in that the situations in which it can be used are limited because it is premised upon a plurality of correctly associated points already existing.

SUMMARY OF THE INVENTION

According to one aspect of the present invention, there is provided an image processing apparatus, which comprises: an obtainment unit configured to obtain, in both a first image obtained by capturing an object and a predetermined space including the object, a corresponding feature part of the object; a specification unit configured to specify a first point on the first image and a second point on the predetermined space; a calculation unit configured to, based on a positional relationship between the first point on the first image and the feature part of the object on the first image, and a positional relationship between the second point on the predetermined space and the feature part of the object on the predetermined space, calculate a degree of matching between the first point and the second point; and a display control unit configured to cause a display unit to display the calculated degree of matching.

Further features of the present invention will become apparent from the following description of exemplary embodiments (with reference to the attached drawings).

BRIEF DESCRIPTION OF THE DRAWINGS

FIG. 7 is a view for describing an example of a degree of matching calculation method in the second embodiment.

DESCRIPTION OF THE EMBODIMENTS

Hereinafter, embodiments of an image processing apparatus according to the present invention will be described in detail in accordance with the accompanying drawings. However, the scope of the present invention is not limited to the examples that are shown.

First Embodiment

An image processing apparatus in the present embodiment calculates and displays a degree of matching of two points (a first point and a second point) in two images (a first image and a second image) that a user designated, the degree of matching indicating the degree to which the points are a pair of corresponding points. The points are specified by designations of a user. The degree of matching is calculated based on a positional relationship of a position of the first point and the second point and a position of a feature part of an object obtained from the first image and the second image respectively. Specifically, in the present embodiment, the degree of matching is calculated based on a distance value with respect to the feature part of the object obtained from the first image and the second image respectively for the first point and the second point. The present image processing apparatus is capable of calculating the degree of matching by using only a feature part of an object, unlike the technique of Japanese Patent Laid-Open No. 2016-21998 in which a plurality of already associated points are required in order to calculate the degree of matching. Note, two points—"a point of interest on a first image (a first point)" and "a point on a second image that corresponds to the point of interest (a second point)"—are referred to as "a pair of corresponding points" in the following description. Also, two points that a user designates as candidates for a pair of corresponding points are referred to as "a pair of corresponding point candidates". The user can interactively confirm the degree of matching of the designated pair of corresponding point candidates. For this reason, in a case in which points are determined to be a mismatch, it is possible to re-input the pair of corresponding points at more appropriate positions. In the present embodiment, the first image and the second image are assumed to be images of a breast, where the same patient is captured at different orientations. In this example, the second image corresponds to a predetermined space including the object. Hereinafter, configuration and processing of the present embodiment is described using FIGS. 1 through 4.

Figure 1:
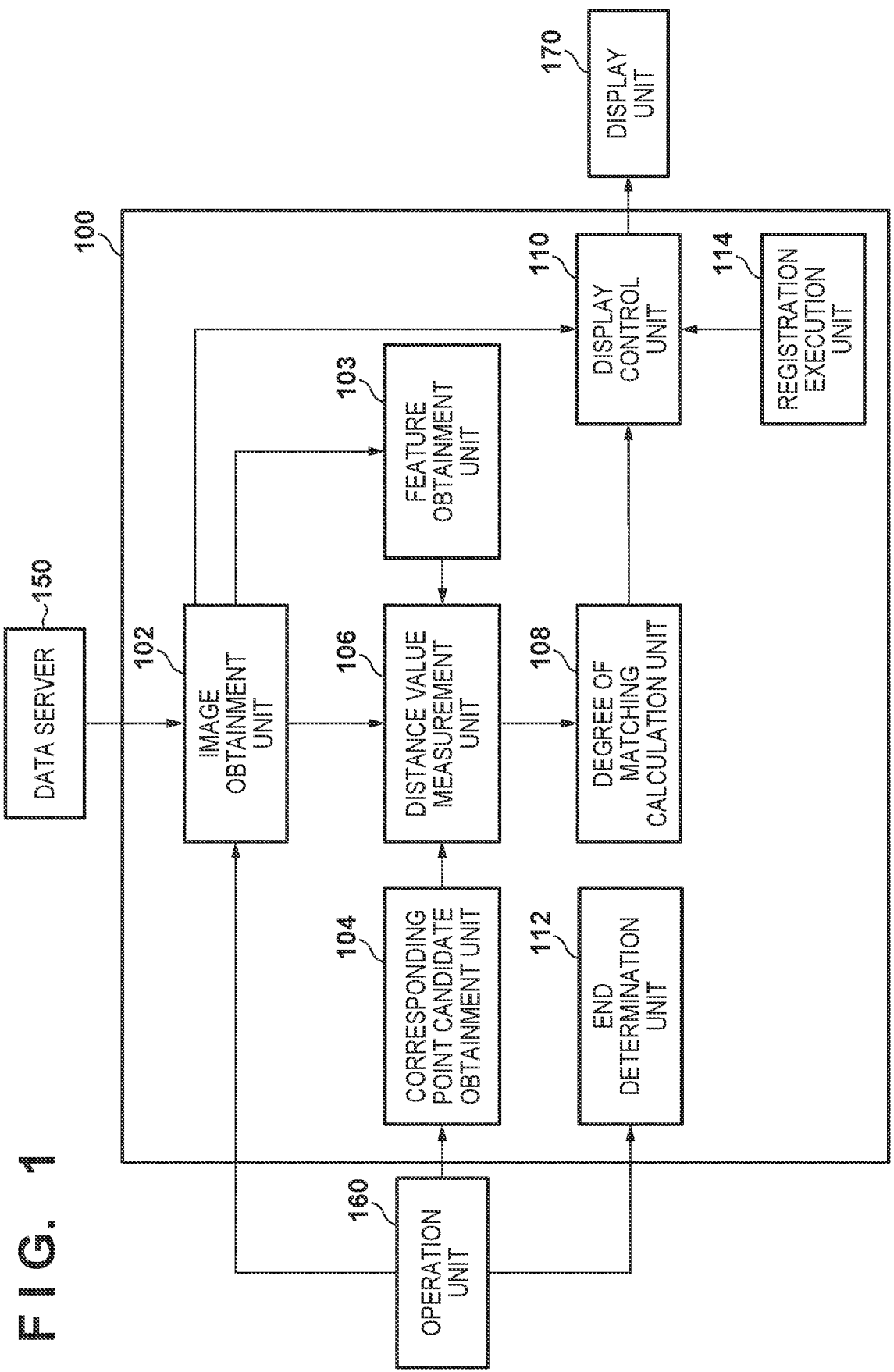
FIG. 1 is a view illustrating a device configuration of an image processing apparatus in a first embodiment.

FIG. 1 describes a configuration of an image processing system in the present embodiment. An image processing apparatus 100 in the present embodiment is connected to a data server 150, an operation unit 160, and a display unit 170 as illustrated in the figure.

The first and the second images that the data server 150 holds are three-dimensional tomographic images obtained by capturing an object in advance under different conditions (such as different modalities, capturing modes, dates, and postures). Modalities that capture a three-dimensional tomographic image may be an MRI apparatus, an X-ray CT apparatus, a three-dimensional ultrasonic image capturing apparatus, a photoacoustic tomography apparatus, a PET/SPECT, an OCT apparatus, and the like. Configuration may be taken such that the first and the second images are captured at the same time by different modalities or different capturing modes for example. The first and the second images may be images in which the same patient is captured at different dates for a follow-up observation by the same modality and in the same posture. Note, the first and the second image are configured as a set of two-dimensional tomographic images, and the position and the orientation of each of the two-dimensional tomographic images are assumed to be stored in the data server 150 after being transformed to a reference coordinate system (a coordinate system within a space based on the object). The first and the second images represented by the reference coordinate system are inputted to the image processing apparatus 100 via an image obtainment unit 102.

The operation unit 160 accepts an operation of a mouse, a keyboard, or the like by the user, and then performs an input in accordance with the operation to the image processing apparatus 100. For example, the operation unit 160 inputs a pair of corresponding point candidates that the user designated to the image processing apparatus 100 via a corresponding point candidate obtainment unit 104. Also, the operation unit 160 inputs a determination of whether or not to end corresponding point specification processing to the image processing apparatus 100 via an end determination unit 112. Further, the operation unit 160 performs a predetermined input to the image obtainment unit 102. The corresponding point candidate obtainment unit 104 and the image obtainment unit 102 respectively can perform processing in accordance with the accepted input in relation to each connected functional unit.

The display unit 170 displays various information such as a display image or degree of matching information that the image processing apparatus 100 generates. Also, a GUI (Graphical User Interface) for obtaining an instruction from the user is also arranged on the display unit 170.

The image processing apparatus 100 is configured by the configuration elements described below. The image obtainment unit 102 obtains the first and the second images inputted to the image processing apparatus 100. A feature obtainment unit 103 obtains a feature part of the object such as the nipple position or the body surface from each of the first image and the second image. The corresponding point candidate obtainment unit 104 obtains the pair of corresponding point candidates (pair of three-dimensional coordinates) on the first image and the second image according to an instruction of the user. Also, the corresponding point candidate obtainment unit 104 adds, in accordance with an instruction of the user, the pair of corresponding point candidates to a corresponding point group stored in the storage unit (not shown). A distance value measurement unit 106 measures a distance value from a corresponding point candidate to a feature part of the object in each of the first image and the second image. Details of this processing are discussed in the description of step S2030 in FIG. 2. A degree of matching calculation unit 108 calculates the degree of matching of the pair of corresponding point candidates based on the distance values from a corresponding point candidates to the feature part of the object. Details of this processing are discussed in the description of step S2040 in FIG. 2. A display control unit 110 performs control for causing information relating to cross-sectional images of the first and the second images and the degree of matching to be displayed on the display unit 170. The end determination unit 112 performs, according to an instruction of the user, a determination of whether or not to end association. A registration execution unit 114 executes a registration between the first image and the second image by using a corresponding point group stored in the storage unit (not shown). Then, a registration result (deformation field and deformation image) is stored in the storage unit (not shown).

Figure 2:
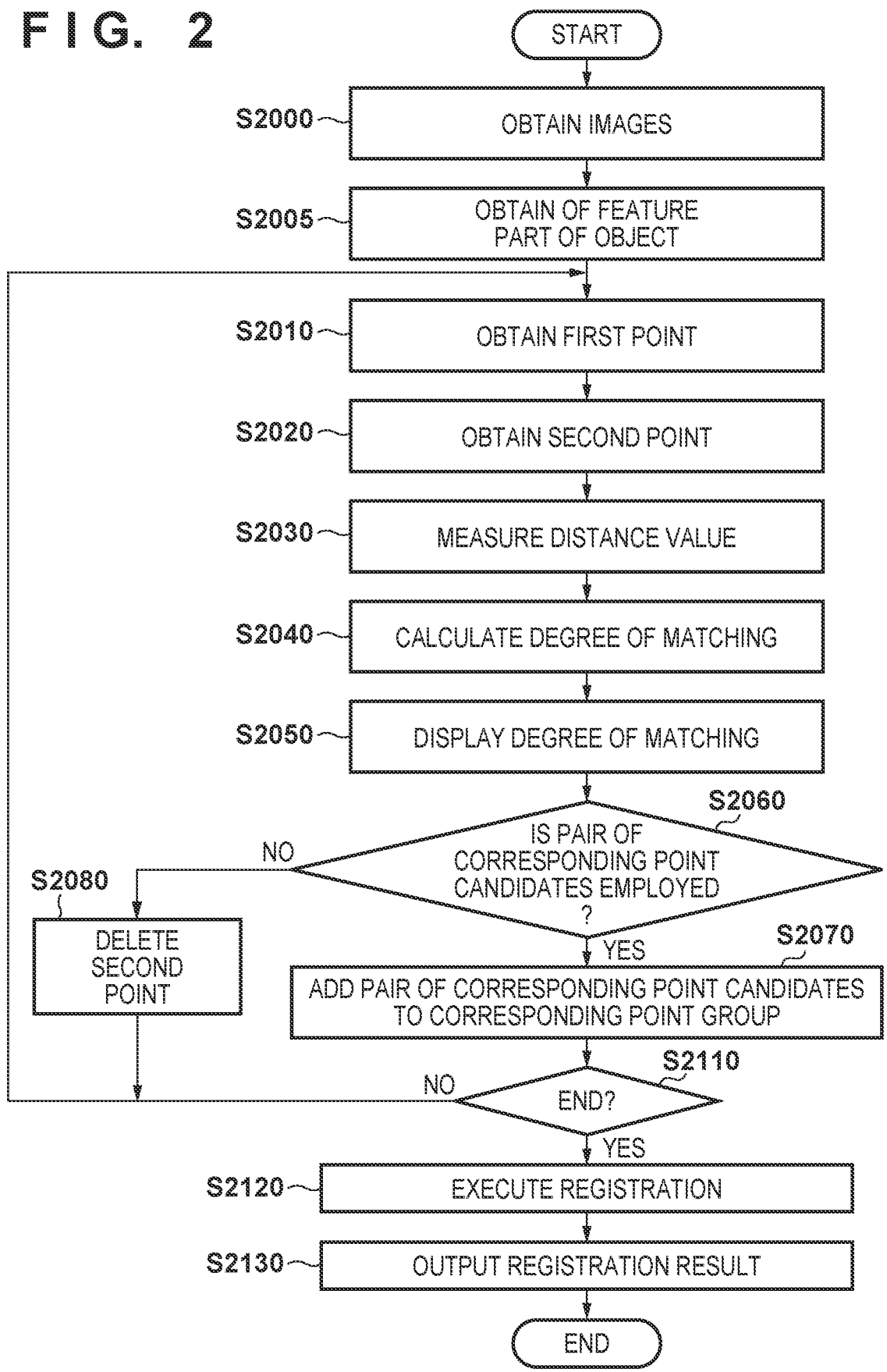
FIG. 2 is a flow diagram illustrating an entire processing procedure in the first embodiment.

FIG. 2 is a flowchart describing an overall processing procedure performed by the image processing apparatus 100.

(Step S2000) (Obtainment of Images)

The image obtainment unit 102 obtains the first image and the second image from the data server 150 in step S2000. Then, obtained information is outputted to the feature obtainment unit 103 and the display control unit 110.

(Step S2005) (Obtainment of a Feature Part of an Object)

In step S2005, the feature obtainment unit 103 obtains, from the first image and the second image obtained in step S2000, a feature part of an object (feature part) captured in both the first image and the second image. Then, the feature obtainment unit 103 outputs obtained information to the distance value measurement unit 106.

A method of obtaining the feature part of the object is described here. As previously described, the feature part of the object in the present embodiment indicates two types of information: a nipple position and a body surface. Firstly, the feature obtainment unit 103 uses a publicly known edge detection algorithm such as a Canny edge detector to detect a plurality of edges within the images. Also, a curved surface that smoothly connects the result of removing edges that are isolated, out of the plurality of detected edges, is assumed to be the body surface. After this, the feature obtainment unit 103 selects and obtains the nipple position from the body surface according to an instruction of the user. Note, the body surface used in the present embodiment is assumed to be a set of points in which the body surface of the breast is sampled in fixed intervals. Hereinafter, this point group is referred to as the body surface point group.

Although description is given of an example of a case in which the body surface is automatically obtained based on the edge detection in the present embodiment, configuration may be taken to obtain the body surface based on a manual operation according to an instruction by the user. For example, in a case where several points on the body surface are sparsely inputted by an instruction by the user, the feature obtainment unit 103 may use an implicit polynomial (Implicit function: IP) to calculate a curved surface that smoothly connects these points. Note, a user instruction such as a specification of the nipple position or a specification of a point on the body surface can be accomplished by the operation unit 160 accepting an operation such as a mouse click from the user on an image in which particular cross-sectional images of the first image and the second image are displayed on the display unit 170. Note, the method of obtaining the feature part of the object is not limited to this and configuration may be taken in which, this information is stored in advance in the data server 150 as additional information of the first image and the second image and the feature obtainment unit 103 obtains this from the data server 150.

(Step S2010) (Obtainment of First Point)

The corresponding point candidate obtainment unit 104 obtains a position (three-dimensional coordinate) of a point of interest (first point) in the first image according to an instruction of the user in step S2010. Specifically, first, the user operates the mouse or the keyboard to select a cross-sectional image of interest, and the display control unit 110 causes the display unit 170 to display the selected cross-sectional image as a cross-sectional image of the first image. Then, on the displayed cross-sectional image, the user inputs a position of interest into the image processing apparatus 100 as a point of interest by performing an operation such as a click of the mouse button or a key press of the keyboard. The corresponding point candidate obtainment unit 104 uses the position and the orientation of the cross-sectional image for the first image to transform the position of interest specified on the cross-sectional image into a position of the point of interest on the reference coordinate system. Note, configuration may be taken in which a point of interest candidate is automatically extracted from the first image by image feature point extraction processing such as an interest operator, and a point at which a feature amount is highest and that has not been selected as the first point up until now is selected. Alternatively, configuration may be taken in which the user selects the point of interest from among point of interest candidates similarly extracted.

Note, in a case in which the first point has already been obtained, the corresponding point candidate obtainment unit 104 can, according to an instruction by the user, move the position of the first point, delete the point, and return to a state in which the first point had not yet been obtained. A move or deletion of a point is performed by the user performing an operation such as a click of the mouse button or a key press of the keyboard similarly to the case in which a point is inputted. For example, it is assumed that, in a case where the mouse is operated to drag the first point on the first image, an instruction of "moving" the first point to the drag destination is provided. Also, it is assumed that, in a case where the mouse is operated to click the first point and a Delete key on the keyboard is pressed after this, an instruction of "deleting" is given. In a case where the first point is deleted, the processing step returns to a state of the time of the start step S2010, and the corresponding point candidate obtainment unit 104 accepts an instruction from the user to obtain a position of a new first point.

The corresponding point candidate obtainment unit 104, in a state in which the first point has already been inputted on the first image, ends the processing of this step in a case where the mouse cursor is on the second image. Then the processing is advanced to step S2020.

(Step S2020) (Obtainment of Second Point)

In step S2020, the corresponding point candidate obtainment unit 104 according to an instruction of the user obtains, on the second image, the position (three-dimensional coordinates) of a candidate of a point (second point) corresponding to the point of interest (first point) obtained in step S2010. Unlike step S2010, it is assumed that the second point is obtained by simply indicating a position on the second image by a pointer such as a mouse cursor (mouse pointer) or a crosshair cursor without an explicit operation such as a mouse click or a key press by the user. In such a case, coordinates at which the indicated position is transformed to the position of the point of interest in the reference coordinate system of the second image are obtained as the coordinates of the second point. Then, the obtained first point and second point are outputted to the distance value measurement unit 106 as a pair of corresponding point candidates (pair of three-dimensional coordinates). Note, although description is given of an example in a case in which a position indicated by a mouse cursor or the like is obtained as the second point according to an instruction of the user in the present embodiment, the second point may be automatically calculated. In such a case, for example, a position on the second image at which the degree of similarity with a local image (template) whose center is made to be the first point is the highest can be calculated by template matching, and thereby it is possible to obtain this position as the second point. By such a configuration, it is possible to reduce the operation required of the user.

(Step S2030) (Measure Distance Value)

In step S2030, the distance value measurement unit 106 measures distance values from the first/second points (pair of corresponding point candidates) obtained in step S2010 and step S2020 to the feature part of the object obtained in step S2005. Then, the distance value measurement unit 106 outputs the measured distance value to the degree of matching calculation unit 108.

In the present embodiment, two types of information (the nipple position and the body surface point group) are obtained as the feature part of the object. Accordingly, for each of the first image and the second image, the distance value measurement unit 106 in the present embodiment calculates two distance values: from the corresponding point candidate position to the nipple position and from the corresponding point candidate position to the body surface point group.

Figure 3A:
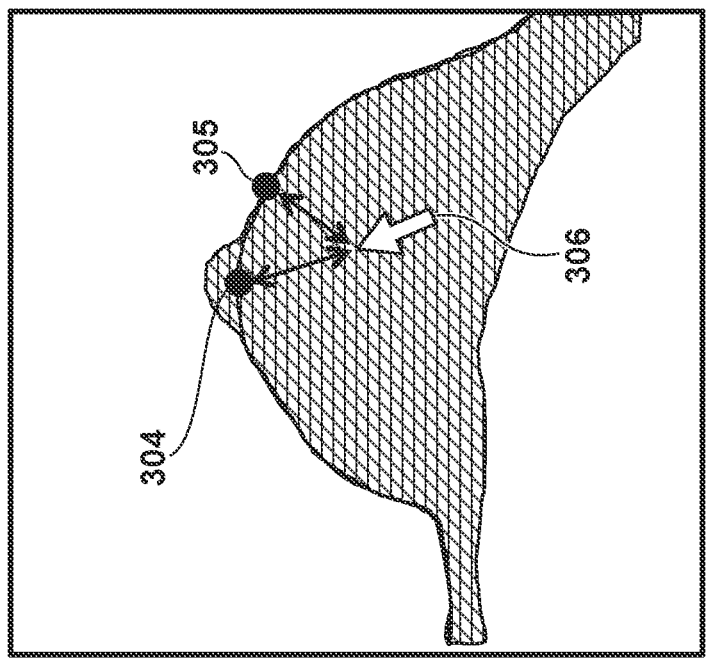
FIGS. 3A and 3B are views illustrating an example of a degree of matching calculation method in the first embodiment.
Figure 3B:
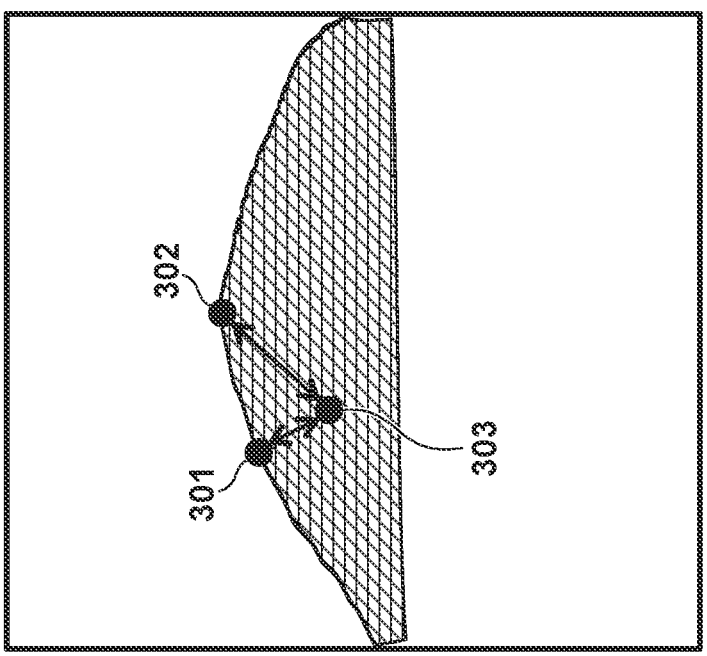

Description is given regarding the calculation of the distance values using FIGS. 3A and 3B. FIGS. 3A and 3B are views illustrating an example of a degree of matching calculation method in the present embodiment. FIG. 3A is assumed to represent the first image, and FIG. 3B is assumed to represent the second image. Note, although each point (corresponding point candidate, nipple position, body surface nearest neighbor point) is positioned on the same plane because the figure is simplified in FIGS. 3A and 3B, in reality, it is not necessary that each point necessarily exists on the same plane.

In the first image, a distance from a corresponding point candidate position to the nipple position is a three-dimensional distance value from a first point 303 to a nipple position 302 of the first image. Also, the distance value from the corresponding point candidate position to the body surface point group is a distance value of a nearest neighbor point in relation to the corresponding point candidate position out of the body surface point group. In the first image, a distance from a corresponding point candidate position to the body surface point group means a three-dimensional distance value from the first point 303 to a nearest neighbor point 301 in the body surface point group of the first image. The same is also true for the second image. Specifically, in the second image, the distance from the corresponding point candidate position to the nipple position is a three-dimensional distance value from a second point 306 to a nipple position 304, and the distance from the corresponding point candidate position to the body surface point group is a distance from the second point 306 to a nearest neighbor point 305 on the body surface point group. The distance value measurement unit 106 calculates these two types of distance values in each of the first image and the second image.

(Step S2040) (Calculate Degree of Matching)

In step S2040, the degree of matching calculation unit 108 calculates a degree of matching of the pair of corresponding point candidates by using the distance values from the corresponding point candidate position measured in step S2030 to the feature part of the object. Then, the degree of matching calculation unit 108 outputs the calculated degree of matching to the display control unit 110.

The calculation of the degree of matching is based on that prior knowledge that in a breast, a change of a distance from a particular position within a breast region to the nipple position and a distance to the body surface is small even if a deformation state is changed. Specifically, the degree of matching calculation unit 108 calculates that the degree of matching is high when the distance values from the corresponding point candidate position to the nipple or from the corresponding point candidate position to the body surface are approximately the same between the first image and the second image, and that the degree of matching is low in a case where there is a large difference. The degree of matching calculation unit 108 calculates, as degrees of matching, two types of individual degrees of matching: a degree of matching calculated based on a distance to the nipple position (nipple degree of matching), and a degree of matching calculated based on a distance to the body surface point group (body surface degree of matching). Also, the degree of matching calculation unit 108 calculates an integrated degree of matching in which the two types of individual degrees of matching are integrated.

A calculation method of the degree of matching is specifically described. Firstly, the degree of matching calculation unit 108 calculates a ratio of the distance value in the first image and the distance value of the second image. The ratio of the distance values to the nipple and the ratio of the distance values to the body surface point group are provided by the following equations respectively.

$$r^{nipple} = \mathrm{dist}(p_{nipple}^2, p_{input}^2) / \mathrm{dist}(p_{nipple}^1, p_{input}^1) \quad \text{(Equation 1)}$$

$$r^{surface} = \mathrm{dist}(s_{nearest}^2, p_{input}^2) / \mathrm{dist}(s_{nearest}^1, p_{input}^1) \quad \text{(Equation 2)}$$

Here, $p_{nipple}^1$ and $p_{nipple}^2$ are coordinates of the nipple position in the first image and the second image respectively (the nipple positions 302 and 305 in FIGS. 3A and 3B). $s_{nearest}^1$ is a nearest neighbor point with respect to the first point out of the points on the body surface point group and $s_{nearest}^2$ is a nearest neighbor point with respect to the second point out of the points on the body surface point group (nearest neighbor points 301 and 304 on the body surface point group in FIGS. 3A and 3B). $p_{input}^1$ and $p_{input}^2$ are a first point and a second point respectively (the first point 303 and the second point 306 in FIGS. 3A and 3B). dist represents a distance value, calculated in step S2030, between the two points. Specifically, these equations refer to a ratio of a distance from the second point to the nipple in the second image with respect to a distance from the first point to the nipple in the first image (Equation 1), and a ratio of a distance from the second point to the body surface point group in the second image with respect to a distance from the first point to the body surface point group in the first image (Equation 2).

Next, the degree of matching calculation unit 108 maps distance ratios $r^{nipple}$ and $r^{surface}$ calculated by the above equations to a degree of matching C of 0.0 to 1.0 according to the following equation.

$$C = \begin{cases} 0.0 & (r < 0.5, \, 2.0 < r) \\ r & (0.5 \le r < 1.0) \\ -1.0 \times (r - 2.0) & (1.0 \le r \le 2.0) \end{cases} \quad \text{(Equation 3)}$$

Figure 4:
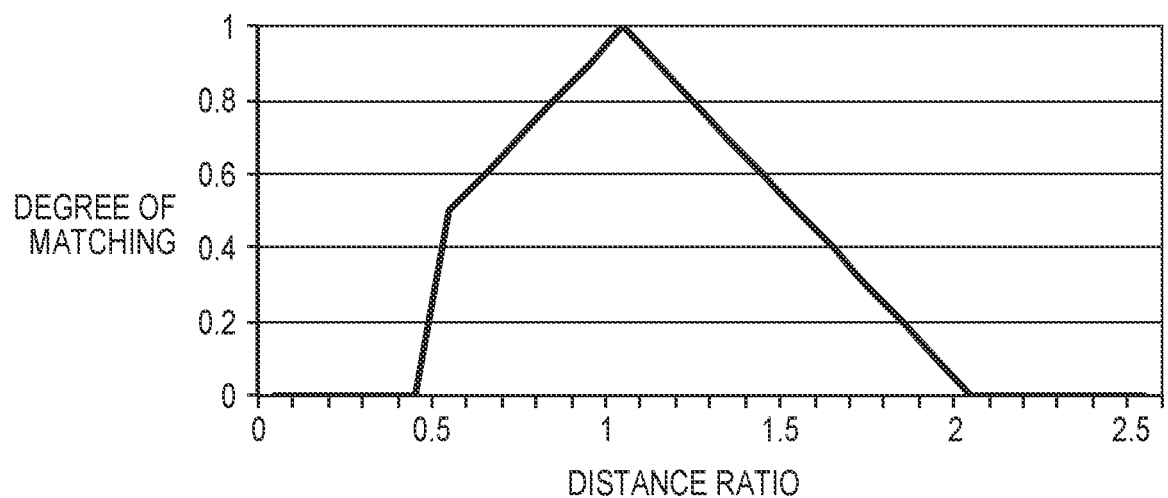
FIG. 4 is a view illustrating a degree of matching in the first embodiment.

FIG. 4 illustrates a degree of matching in the present embodiment. Specifically, FIG. 4 is a graphing of the above equation. As illustrated in the same figure, the degree of matching is a maximum value of 1 when a point-to-point distance of the nipple is the same (specifically the distance ratio is 1) and linearly decreases the more the distance ratio separates from 1. Also, a value of the degree of matching becomes 0 in a case where the distance ratio is smaller than 0.5 or in a case where it is larger than 2.0.

Note, in the present embodiment, as illustrated in FIG. 4, description is given of an example of a case where a change of the degree of matching associated with a change of the distance ratio is connected by a straight line (specifically linear), however, a relationship where the change is connected by a curved line (specifically nonlinear) is also possible. In such a case, it is possible to design a more flexible function that moderates reduction of the degree of matching in the vicinity of a distance ratio of 1.0. Also, other than the method based on ratios of the distance values from the corresponding point candidate position to the feature parts of the object as described above, another method based on a comparison of the distance values from the corresponding point candidate position to the feature parts of the object may be used for calculation of the degree of matching. For example, the degree of matching may be calculated based on a difference of the distance values. In such a case, the degree of matching becomes 1 in a case where a difference of the distance values is 0 and the degree of matching becomes 0 in a case where a difference of the distance values is greater than or equal to a predetermined threshold value, and it is possible to transform the difference of the distance values to a degree of matching by using a transformation function so that intervals therebetween are connected linearly.

Finally, the degree of matching calculation unit 108 calculates an integrated degree of matching in which each of the individual calculated degrees of matching are integrated. The integrated degree of matching is calculated as an average or a weighted average of individual degrees of matching, or a product of the individual degrees of matching for example. Note, configuration may be taken such that the method of a degree of matching can be selected by the user. In particular, configuration may be such that the user can set a weighting in a case where a weighted average is used. Note, configuration may be such that a calculation of the integrated degree of matching may not be performed in a case where the integrated degree of matching is not displayed by the processing of step S2050.

(Step S2050) (Display Degree of Matching)

In step S2050, the display control unit 110 performs control for displaying the degree of matching calculated in step S2040 to the display unit 170. The display control unit 110 is equipped with a plurality of degree of matching display methods, and can select any from among these display methods or can combine the plurality of display methods in a display.

Figure 5:
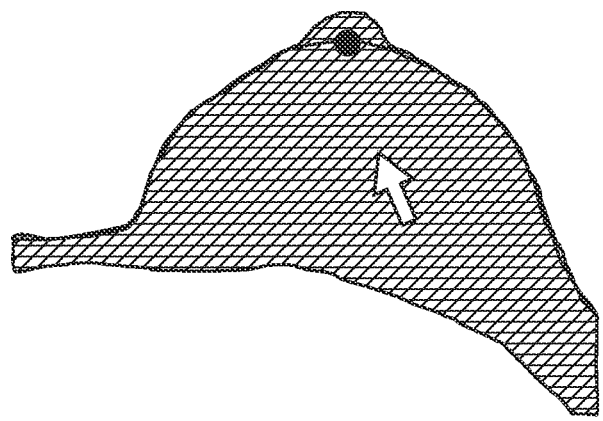
FIG. 5 is a view illustrating an example of a display of a degree of matching in the first embodiment.

FIG. 5 illustrates an example of a display of a degree of matching in the present embodiment. An example in which character information and symbol information are combined in a display of a degree of matching is illustrated in FIG. 5. The nipple degree of matching being 0.67 and the body surface degree of matching being 0.11 can be read from a character sequence in the top portion of the display in FIG. 5. However, it is more convenient to be able to more intuitively confirm the degree of matching in a case where the user observers a change of a value of the degree of matching in real time while moving the mouse cursor. For this reason, a display by symbol information in addition to character information is also performed. A display comprising black circles (●) and x-marks (×) corresponds to a display by the symbol information. Black circles and x-marks are chosen as indicators comprising 10 graduations and a degree of matching is indicated by a number of black circles. Specifically, it is indicated that a value of the degree of matching is between 0.6 to 0.7 in a case where six black circles are seen. Although a display by symbol information is performed by using black circles (●) and x-marks (×) in the example of FIG. 5, configuration may be taken in which an indicator is rendered as a graphic. The user can intuitively know the value of the degree of matching more simply than with a numerical value of the degree of matching shown by performing a display by symbol information or a display by a graphic.

Also, it is possible to also display the degree of matching by a text color. In such a case, in combination with a magnitude of the degree of matching, a text color of text describing the degree of matching is caused to change in FIG. 5. The color is green, for example, in a case where the degree of matching is high (close to 1.0), and the color is red, for example, in a case where it is low (close to 0.0). With such a configuration, the user can more intuitively know the value of the degree of matching (indicator) than with indication by symbol information. Also, configuration may be such that the display color of the mouse cursor or the crosshair cursor is changed in accordance with the degree of matching. Note, in such a case, it may be established in advance which display colors are set based on the degree of matching (to the integrated degree of matching for example), and configuration may be taken such that the user can set these. Also, the degree of matching may be presented by sound instead of an image.

Such methods of displaying the degree of matching may be used in combination rather than using just one. For example, it is possible that character information, symbol information, and character colors are used together. Also, in a case where a plurality of display methods are used in combination, an effect of being able to intuitively know the degree of matching and an effect of being able to observe the value of the degree of matching in detail are combined.

Also, although FIG. 5 illustrates an example in which both the nipple degree of matching and the body surface degree of matching are simultaneously displayed, configuration may be taken in which one is not displayed or in which they are displayed separately. Also, the integrated degree of matching may be also displayed at the same time as these individual degrees of matching. Also, configuration may be taken to only display the integrated degree of matching. Configuration may be taken in which the user can set which degree of matching will be displayed.

(Step S2060) (Determination of whether to Employ a Pair of Corresponding Point Candidates)

In step S2060, the corresponding point candidate obtainment unit 104 obtains an instruction from the user of whether or not to employ a pair of corresponding point candidates as a pair of corresponding points, and performs processing that branches the processing thereafter in accordance with this. In a case where the pair of corresponding point candidates are employed (Yes in step S2060), the image processing apparatus 100 advances the processing to step S2070. In a case where the pair of corresponding point candidates are not employed (No in step S2060), the image processing apparatus 100 advances the processing to step S2080.

A method for specifying that the pair of corresponding point candidates are/are not employed is illustrated below. In the present embodiment, as described in the description of the processing of step S2020, a method for simply indicating the position on the second image by a mouse cursor or a crosshair cursor is used as a method for obtaining the second point. Here it is assumed that an instruction to "employ" is given in a case where the user does not move the cursor from the position and clicks the mouse or presses a key, for example. Meanwhile, it is assumed that an instruction of "do not employ" is given in a case where the cursor is moved to a different position without performing a click or a key press.

(Step S2070) (Add to a Corresponding Point Group the Pair of Corresponding Point Candidates)

In step S2070, the corresponding point candidate obtainment unit 104 finalizes the pair of corresponding point candidates as corresponding points and adds them to a corresponding point group stored in the storage unit (not shown). Then, the processing is advanced to step S2110.

(Step S2080) (Delete Second Point)

In step S2080, the image processing apparatus 100 deletes information of the second point obtained in step S2020. By this, the image processing apparatus 100 enters a state in which only the first point is obtained and the second point is not obtained yet. Then, the image processing apparatus 100 advances the processing to step S2010 and repeats the processing subsequent thereto.

(Step S2110) (End Determination)

In step S2110, the end determination unit 112 performs a determination of whether or not to end the corresponding point candidate specification processing. For example, an end instruction that the user inputted is obtained by an end button arranged on the display unit 170 being clicked or the like by a mouse. In a case where it is determined that the end determination unit 112 is to be ended (Yes in step S2110), the processing advances to step S2120. Meanwhile, in a case where it is determined that the end determination unit 112 is not to be ended (No in step S2110), the processing returns to step S2010 and the processing from that step is executed again. In a case where there is no input of a re-designation of corresponding point candidates here, the image processing apparatus 100 enters a standby state in a state where a cross-sectional image is displayed until there is an end input.

(Step S2120) (Execute Registration)

In step S2120, the registration execution unit 114 uses information of the corresponding point group finalized as corresponding points in the processing of step S2070 and stored in the storage unit (not shown) to execute a registration between the first image and the second image. If a registration algorithm uses the distance differences of the corresponding point group as the cost, any publicly known method can be used. For example, a method based on a thin plate spline (TPS), a method based on a free form deformation (FFD), or a landmark LDDMM (Large Deformation Diffeomorphic Metric Mapping) is used. The registration execution unit 114 calculates, as a registration result, a deformation field which represents a correspondence between the first image and the second image. Furthermore, the registration execution unit 114 causes at least one of the first image and the second image to deform in order to generate a deformation image that is registered with the other image. The registration execution unit 114 stores this information to the storage unit (not shown).

Note, although in the present embodiment description is given of an example of a case in which a registration is performed based on only information of the corresponding point group stored in the storage unit (not shown), a registration may also be performed based on the first image and the second image. In such a case, a degree of similarity between images may be used in addition to a distance difference of the corresponding point group as a cost.

(Step S2130) (Output Registration Result)

In step S2130, the display control unit 110 performs control for displaying information (such as a deformation image or a deformation field) of the registration result obtained in step S2120 to the display unit 170. The above is a flow of processing by the image processing apparatus 100.

According to the flowchart of FIG. 2, the processing loops in the route of step S2020 to step S2060, step S2080, step S2010, and then step S2020 when the mouse cursor moves on top of the second image in a state in which the first point is inputted on the first image (step S2010). The image processing apparatus 100 is able to continue recalculation of the degree of matching while updating the second point in real time by repeating such processing. For this reason, the image processing apparatus 100 is able to search in real time for what vicinity within the space of the second image the degree of matching becomes high. By this, there is the effect that the user can input corresponding points balancing intuitive judgment that the corresponding point is likely to in a particular vicinity and the quantitative index of the degree of matching.

Note, although a case in which a breast is an object, and a nipple position and a body surface shape are used as feature parts of the object is exemplified in the present embodiment, limitation is not made to this. For example, a barycenter position of a lesion or a bifurcation position of a major blood vessel may be used as a feature part of the object. Also, plurality of points or a plurality of surface shapes may be used together rather than a combination of one point (nipple position) and one surface shape (body surface shape) as in the present embodiment. With such a configuration, two or more types of feature parts of an object can be used.

Also, the object may be a site other than a breast. For example, in a case where the object is a pelvis, the same effect can be obtained by using, as a feature part of the object, a point of an anatomical feature existing on the surface of the pelvis, such as the anterior superior iliac spine. Note that the image processing apparatus 100 itself need not know what the object is, and need not know what to use as an object feature part, so long as it is provided with information indicating whether the feature part of the object is a point or a surface shape. Specifically, for an arbitrary object, the user can cause the image processing apparatus 100 to operate by using a feature part of an (hypothetical) object determined to have fixed invariability in relation to deformation.

First Variation of the First Embodiment (Calculating a Degree of Matching by Considering a Degree of Reliability)

In the present embodiment description is given of an example of a case in which a degree of matching is calculated based on only the distance values measured in step S2030, however, configuration may be taken in which other information is taken into consideration. For example, introducing "a degree of reliability" element, weighting may be performed such that a region in which a degree of reliability within an image region is high has a higher degree of matching, and a region in which a degree of reliability is low has a lower degree of matching.

A distance value from a body surface is given as an example of a degree of reliability. Regarding the knowledge that even if there is a deformation in the breast, a distance from a nipple or a distance from a body surface will not change, which is the premise of the degree of matching calculation, it is considered that this will cease to hold the more separated (deeper) the position of the corresponding point candidate is from the body surface. Accordingly, a region in which the distance value from the body surface is small is set to have a higher degree of reliability and a region in which the distance value is larger is set to have a low degree of reliability.

In such a case, in step S2005, the feature obtainment unit 103 uses the body surface calculated for the first image and the second image respectively to further calculate "a body surface distance transformation image". This is a three-dimensional image in which the shortest distance to the body surface is stored as a voxel value for each voxel in the image region. Also, in a case where the degree of matching is calculated in step S2040, firstly, the degree of matching calculation unit 108 calculates degree of reliability coefficients $R^1$ and $R^2$ in accordance with the following equation with respect to the first image and the second image respectively.

$$R^1 = \begin{cases} -\dfrac{dist(s^1_{nearest}, p^1_{input})}{d_{th}} + 1 & (dist(s^1_{nearest}, p^1_{input}) < d_{th}) \\ 0 & (dist(s^1_{nearest}, p^1_{input}) \geq d_{th}) \end{cases} \quad \text{(Equation 4)}$$

$$R^2 = \begin{cases} -\dfrac{dist(s^2_{nearest}, p^2_{input})}{d_{th}} + 1 & (dist(s^2_{nearest}, p^2_{input}) < d_{th}) \\ 0 & (dist(s^2_{nearest}, p^2_{input}) \geq d_{th}) \end{cases}$$

Here, $d_{th}$ is a threshold value for the distance to the body surface, and the degree of reliability (coefficient) becomes 0 in a case where the distance is larger than this value. Here, although description is given of an example of a case in which the degree of reliability coefficients $R^1$ and $R^2$ linearly attenuate the larger the distance value is from the body surface, a function of another form may be used. For example, in a case where there is prior knowledge that the relationship between the distance from the body surface and the degree of reliability follows a normal distribution, it is possible to directly represent this prior knowledge by calculating the degree of reliability coefficient by a half gaussian function in which the average value is 0.

Then, the degree of matching calculation unit 108 performs a weighting of a degree of matching C obtained in Equation 3 according to the following equation by using $R^1$ and $R^2$ to calculate C'.

$$C' = C \times R^1 \times R^2 \quad \text{(Equation 5)}$$

This equation defines the product of the degree of reliability coefficient in each image ($R^1$ and $R^2$) as a degree of reliability of a degree of matching, and obtains the degree of matching C' after correction by using this degree of reliability as a correction coefficient for integrating the degree of matching C. Note, although description is given of an example of a case in which the product of the degrees of reliability is used in (Equation 5), a formula other than (Equation 5) may be performed. For example, the average value of $R^1$ and $R^2$ may be used as the degree of reliability of the degree of matching. Specifically, configuration may be taken such that the degree of matching C' after correction is calculated by the product of the average value of $R^1$ and $R^2$ and the degree of matching C. When one degree of reliability becomes 0, the degree of matching becomes 0 irrespective of the value of the other degree of reliability in a case where the product of the degree of reliability is used as in (number 5), however such an extreme tendency can be mitigated by using the average value. Also, it is possible to use only one of $R^1$ and $R^2$ as the degree of reliability of the degree of matching. In such a case, C' may be calculated by multiplying either $R^1$ and $R^2$ with C. Note, which degree of reliability coefficient is used as the degree of reliability of the degree of matching may be predetermined and may be selected in accordance with the input image. For example, it is possible to use only the image having a higher body surface extraction accuracy as the degree of reliability calculation target.

In this way, by virtue of the present variation, it becomes possible to apply knowledge of the reliability of the degree of matching to the calculation of a degree of matching.

Second Variation of the First Embodiment (Further Calculating a Degree of Matching Based on a Geodesic Distance of a Nipple and a Body Surface Nearest Neighbor Point)

Although the calculated degree of matching is only something based on distance from a corresponding point candidate to a feature part of an object in the present embodiment, configuration may be taken in which a calculated degree of matching is additionally included rather than use a corresponding point candidate directly. For example, a geodesic distance between the nearest neighbor point 301 on the body surface point group (and the nearest neighbor point 305 on the body surface point group) and the nipple position 302 (and the nipple position 304) in FIGS. 3A and 3B may be measured and a degree of matching calculated based on the distance value may be additionally included. In such a case, it can be expected that the reliability of the degree of matching will improve because the measured distance value is not influenced by the depth from the body surface of the corresponding point candidates. Note, a rectilinear distance of a nearest neighbor point on the body surface point group and a nipple position may be used in place of the geodesic distance as an approximate value.

Third Variation of the First Embodiment

Although registration processing of two images is performed by using an obtained corresponding point group in the present embodiment, configuration may be taken in which registration processing is not required and the image processing apparatus 100 performs only an obtainment and saving of corresponding points. In such a case, the image processing apparatus 100 can be used for various purposes for searching for corresponding points or corresponding sites between images. For example, in a case where a point of interest such as a lesion position on the first image is provided, the image processing apparatus 100 can be used for the purpose of searching for the corresponding lesion in the second image.

Also, although the image processing apparatus 100 uses the two images—the first image and the second image—to perform the processing for calculating the degree of matching between the images in the present embodiment, the second image is not necessary in the embodiment of the present invention. Here, the image processing apparatus 100 can display the degree of matching between a point of interest of the object on the first image obtained preoperatively and a position of interest of the object obtained by measuring a real space intraoperatively (not an image). For example, in a case where a point of interest such as a lesion position on the first image captured preoperatively is provided, the image processing apparatus 100 can present a degree of matching for how much a position (second point) indicated by a pointer in real space intraoperatively is a point corresponding to the point of interest (first point). At that time, it is possible to measure the nipple position or the body surface shape of the object in real space by a three-dimensional position sensor (three-dimensional stylus or distance measurement camera). Also, a puncturing instrument can be used, for example, as a pointer within the real space. Specifically, it is possible to measure the position and the orientation of the instrument by a three-dimensional position sensor and to use the position of the tip of a puncture needle. In this example, the real space including the object corresponds to a predetermined space including the object.

Fourth Variation of the First Embodiment

In the present embodiment, the images used for the calculation of the degree of matching are the same image as the images that the user refers to when designating the first point and the second point, however, configuration may be taken in which the first image and the second image may be deformed and displayed to achieve a display mode in which it is easy for a user to search for corresponding points when designating the first and second points. For example, the image processing apparatus 100 can deform an image (hereinafter referred to as rectangularly deform) so that voxels that have the same depth from the body surface are included in the same plane, and use the result as a display image. For this, it is possible to use the technique of Japanese Patent Laid-Open No. 2015-130972, for example. Accordingly, it is possible to cause the efficiency of obtainment of corresponding point candidates (first point and second point) to improve because it is possible to observe blood vessels running at the same depth from the body surface in a breast image even without switching the slice of the image.

Here, although a rectangularly deformed image is preferred for an observation of corresponding points, it is a distorted image on which a nonlinear deformation is applied and does not maintain a physical positional relationship in the original image. Accordingly, in the present variation, an obtainment of corresponding point candidates is performed by using a rectangularly deformed image, and the degree of matching calculation is performed on the original image before the deformation. Specifically, the corresponding point candidate obtainment unit 104 performs a coordinate transformation of corresponding point candidates (third point and fourth point) inputted on the first and second rectangularly deformed images to calculate the points (first point and second point) on the first image and the second image. Here, a coordinate transformation is performed by applying, to the third and fourth points, an inverse function of the deformation function used when the rectangularly deformed images are generated. Then, the degree of matching is calculated by using the coordinates (specifically, the coordinates of the first point and the second point) in the image space after transformation. Note, the method of generating the deformation image is not limited to a rectangular transformation, and any method for easily making a comparison between images may be used. For example, configuration may be taken in which a deformation image in which points at the same distance from the nipple are positioned on the same plane is generated and displayed.

<Second Embodiment> (Calculating and Displaying a Degree of Matching Map)

The image processing apparatus 100 in the present embodiment supports input of corresponding points by displaying a distribution of the degree of matching with the first point inputted in the first image. The configuration of the image processing system in the present embodiment is the same as in FIG. 1. However, some of the processing details of each unit differ from the first embodiment as described below. Hereinafter, description is given regarding differences from the first embodiment regarding the image processing apparatus 100 according to the present embodiment.

Figure 6:
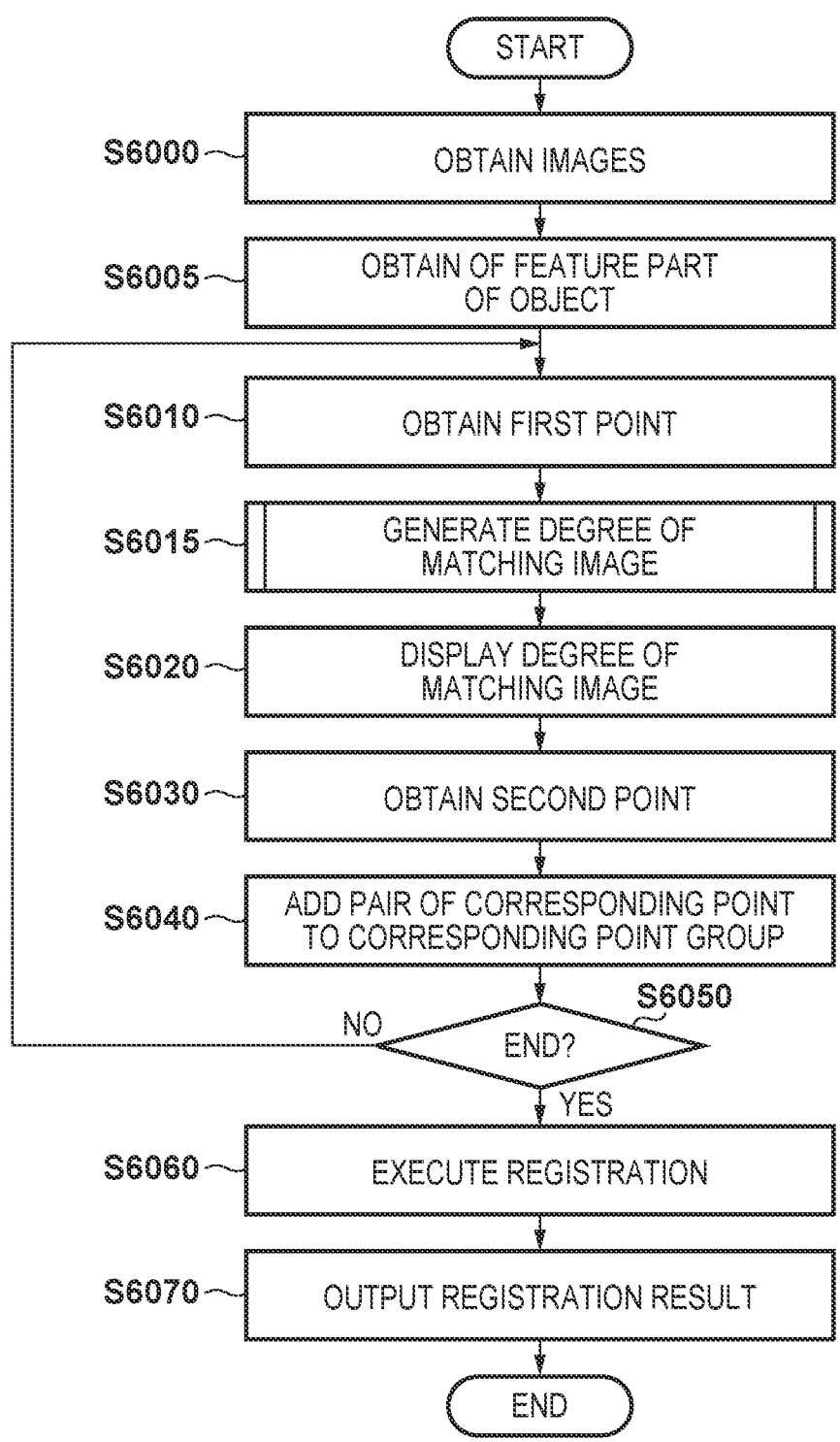
FIG. 6 is a flow diagram for describing an entire processing procedure in a second embodiment.

FIG. 6 is a flowchart describing an example of an overall processing procedure performed by the image processing apparatus 100 in the present embodiment. Note, because the processing of step S6000 to step S6010, step S6040, and step S6050 to step S6070 is the same as the processing of step S2000 to step S2010, step S2070, and step S2110 to step S2130 in FIG. 2, description is omitted.

(Step S6015) (Generation of a Degree of Matching Image)

In step S6015, for each voxel position on the second image, the image processing apparatus 100 calculates the degree of matching when the position is assumed to be a candidate for a point corresponding to a point of interest. Specifically, the image processing apparatus 100 calculates a degree of matching in a case where each voxel position is assumed to be a second point corresponding to the first point (a case where they are assumed to be a pair of corresponding point candidates). Then, the image processing apparatus 100 generates a volume image (hereinafter referred to as a degree of matching image) having a degree of matching at each voxel position as a voxel value. This degree of matching image illustrates a distribution of a degree of matching at each voxel position. Hereinafter, description is given regarding details of the processing of step S6015 by using the flowchart of FIG. 7. FIG. 7 is a flowchart describing an example of detail processing procedure of step S6015 in FIG. 6.

(Step S7000) (Initialization of the Degree of Matching Image)

In step S7000, the degree of matching calculation unit 108 generates and initializes a degree of matching image of the same size as the second image. For example, 0 is set to every voxel of the degree of matching image.

(Step S7010) (Obtain Voxel Position Within the Image)

In step S7010, the corresponding point candidate obtainment unit 104 selects, as the second point, one voxel that has yet to be selected from among the voxels within the second image, and then obtains the position of that voxel (three-dimensional coordinate value). Specifically, a combination between the second point obtained in this step and the first point obtained in step S6010 is made to be a pair of corresponding point candidates. Then, the corresponding point candidate obtainment unit 104 outputs the obtained first point and second point to the distance value measurement unit 106 as a pair of corresponding point candidates (pair of three-dimensional coordinates).

(Step S7015) (Measure Distance Value)

In step S7015, the distance value measurement unit 106 measures the distances from the pair of corresponding point candidates obtained in step S7010 to the feature part of the object obtained in step S6005. This processing can be executed by the same processing as step S2030 in FIG. 2. Also, the distance value measurement unit 106 outputs the measured distance value to the degree of matching calculation unit 108.

(Step S7020) (Calculate Degree of Matching)

Next, in step S7020, the degree of matching calculation unit 108 uses the distance values measured in step S7015 to calculate a degree of matching of the pair of corresponding point candidates. This processing can be executed by the same processing as step S2040 in FIG. 2. Also, the degree of matching calculation unit 108 sets the calculated value to a voxel of a degree of matching image corresponding to the voxel position obtained in step S7010 as a value of the degree of matching at the position. Note, the degree of matching calculation unit 108 may save (set) a plurality of degrees of matching (each individual degree of matching or an integrated degree of matching) to each voxel as vector values, and may save (set) all degrees of matching selected in advance as scalar values.

(Step S7030) (Determination of Completion of Calculation of the Degree of Matching at All Voxel Positions)

Next, in step S7030, the degree of matching calculation unit 108 determines whether or not there is a voxel for which a degree of matching has not been calculated. In a case where the result of this determination is that a calculation of a degree of matching has ended for all voxels, the processing of step S6015 ends. Meanwhile, in a case where there is a voxel for which a degree of matching has yet to be calculated (No in step S7030), the processing returns to step S7010, and the same processing is executed on the remaining voxels. A degree of matching image is generated by the above procedure.

(Step S6020) (Display of a Degree of Matching Image)

Returning to the description of FIG. 6, next, in step S6020, the display control unit 110 performs control for displaying the degree of matching image generated in step S6015 to the display unit 170. Specifically, the display control unit 110 obtains, in the degree of matching image generated in step S6015, the degree of matching of a cross-section corresponding to the cross-sectional image of the second image. Then, the display control unit 110 displays the cross-sectional image of the second image and also causes the display unit 170 to display information of the distribution of the degrees of matching. This display can be of a form in which the distribution of the degrees of matching on the cross-sectional image of the second image represented by shading, for example, is superimposed as a color map (degree of matching map). For example, the display control unit 110 may define in advance a correspondence between the value of the degree of matching and a display color in a table, and superimpose a display color determined in accordance with this table on a voxel position corresponding to the second image. Note, a display/non-display of information of the degree of matching distribution may be selectable in accordance with an instruction of the user. Also, configuration may be taken such that it is selectable in accordance with an instruction of the user regarding whether to display each individual degree of matching or an integrated degree of matching.

Also, the display mode of the degrees of matching distribution is not limited to superimposition of a color map representing the degree of matching. For example, an isopleth of the degrees of matching may be superimposed. The display mode of the degree of matching distribution is not limited to a mode in which it is superimposed on the second image, and configuration may be taken in which an identical cross-section of the degree of matching image is lined up and displayed such that comparison with the second image is easier. These display modes of the distribution of the degree of matching may be selectable in accordance with an instruction of the user.

Figure 8B:
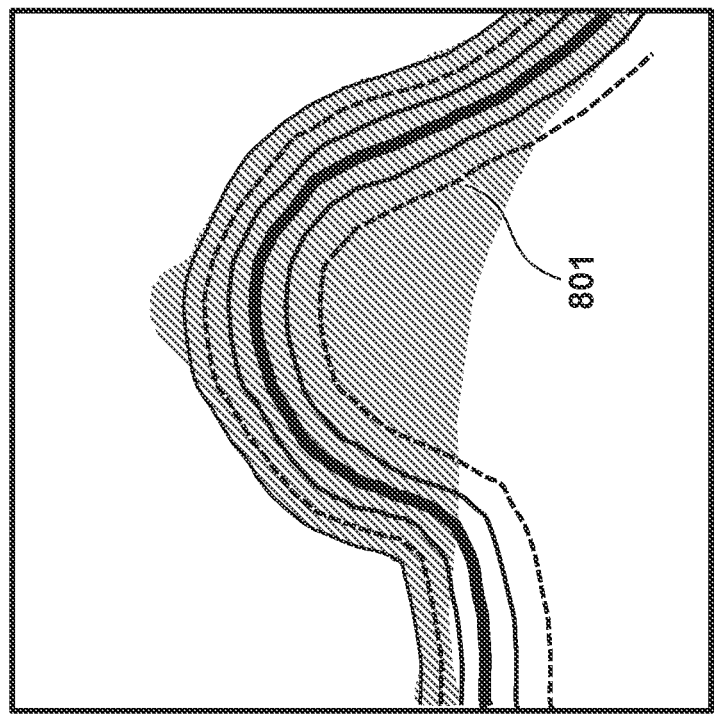
FIGS. 8A and 8B are views illustrating an example of a display of a degree of matching in a third embodiment.
Figure 8A:
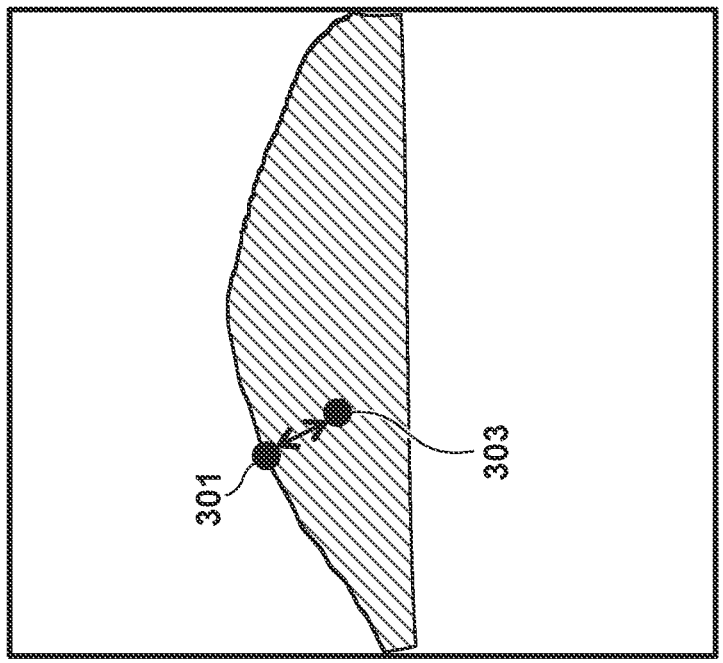

FIGS. 8A and 8B illustrate an example of a display of a degree of matching distribution in the present embodiment. Here, a degree of matching map of a body surface degree of matching is illustrated. FIG. 8A is a view illustrating the first point 303 and the nearest neighbor point 301 on the body surface point group in the first image. FIG. 8B is a view illustrating a result 801 displaying the degree of matching map superimposed onto the second cross-sectional image. In FIG. 8B, isopleths rendered with the thickest lines represent the regions with a highest degree of matching and lower degrees of matching are represented in order of thin lines to dotted lines. In this way, a surface whose distance from the body surface is a value that is equal to the distance between the nearest neighbor point 301 on the body surface point group and the first point 303 in the first image has a highest degree of matching, and the degree of matching is lower the more separated from that distance value it becomes.

(Step S6030) (Obtainment of Second Point)

In step S6030, the corresponding point candidate obtainment unit 104 obtains a position of the second point according to an operation of the operation unit 160 by the user. In step S2020 in FIG. 2 described in the first embodiment, the corresponding point candidate obtainment unit 104 obtains a position simply indicated by a mouse cursor or the like. In contrast to this, in this step, processing to obtain the second point is performed only after an operation of a mouse click or a keyboard by the user is performed first. When the corresponding point candidate obtainment unit 104 obtains the second point, it finalizes the pair of the first point and the second point as corresponding points and adds them to the corresponding point group stored in the storage unit (not shown).

When specification of the second point is performed by the operation of the user, the user, while referencing the degree of matching map that is being displayed on the display unit by the processing of step S6020, inputs a second point at a position whose degree of matching is high and that is thought to be corresponding.

As described above, by virtue of the present embodiment, because the user can confirm a degree of matching distribution, they can easily perform an association while considering the balance between the degree of matching and the correspondence relationship on the image. Also, there is an effect that it is possible to avoid incorrect correspondence of corresponding points even if there are a plurality of positions (local optimal solutions) at which the degree of matching is high, because it is possible to find the position at which the degree of matching is the highest (global optimal solution).

Variation of the Second Embodiment

Although a calculation of degrees of matching at voxel positions corresponding to every voxel of the second image is performed in the embodiment described above, the voxel positions at which the degree of matching is calculated are not limited to this. For example, a calculation of a degree of matching only at voxel positions to which the second image is thinned out by a predetermined interval may be performed, and the degree of matching of the (thinned out) voxel positions at which the calculation of the degree of matching is not performed may be calculated by interpolation. Accordingly, it is possible to perform a calculation of a degree of matching map at a higher speed. Also, in a case where the inside and outside of an object can be determined, configuration may be taken so as to calculate only a degree of matching of voxel positions belonging within the object.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-174964, filed Sep. 7, 2016 which is hereby incorporated by reference herein in its entirety.

What is claimed is:

1. An image processing apparatus, comprising:
a memory storing a program; and
one or more processors which, by executing the program, function as:
an obtainment unit configured to obtain, in a first image and a second image obtained by capturing an object, a feature part of the object;
a specification unit configured to specify a first point on the first image and a second point on the second image;
a calculation unit configured to, based on a positional relationship between the first point on the first image and the feature part of the object on the first image, and a positional relationship between the second point on the second image and the feature part of the object on the second image, calculate a degree of matching between the first point and the second point; and
a display control unit configured to cause a display unit to display the calculated degree of matching,
wherein in a case where a position of the second point on the second image is changed by the specification unit, the calculation unit recalculates, based on the positional relationship between the first point on the first image and the feature part of the object on the first image, and the positional relationship between the second point based on the changed position on the second image and the feature part of the object on the second image, the degree of matching between the first point on the first image and the second point based on the changed position on the second image.

2. The image processing apparatus according to claim 1, wherein the first image and the second image are obtained by capturing the object under different conditions.

3. The image processing apparatus according to claim 2, wherein the one or more processors which, by executing the program, further function as:
a deformation unit configured to deform the first image and the second image to a first deformation image and a second deformation image, respectively; and
a coordinate transformation unit configured to calculate a position of a point on the first image corresponding to a position of a point on the first deformation image, and a position of a point of the second image corresponding to a position of a point of the second deformation image,
wherein the specification unit further specifies a third point on the first deformation image and a fourth point on the second deformation image, and
the calculation unit further calculates, based on a positional relationship between a fifth point on the first image corresponding to the third point and the feature part of the object on the first image and a positional relationship between a sixth point on the second image corresponding to the fourth point and the feature part of the object on the second image, a degree of matching between the fifth point and the sixth point.

4. The image processing apparatus according to claim 1, wherein the calculation unit calculates the degree of matching based on a first distance from the first point on the first image to a position of the feature part of the object on the first image and a second distance from the second point on the second image to a position of the feature part of the object on the second image.

5. The image processing apparatus according to claim 4, wherein the calculation unit calculates the degree of matching based on the first distance, the second distance, and a weight based on the first distance or the second distance.

6. The image processing apparatus according to claim 1, wherein the object is a breast, and the obtainment unit obtains a nipple of the breast or a point on a body surface of a breast as the feature part of the object.

7. The image processing apparatus according to claim 1, wherein the obtainment unit obtains two or more types of feature parts of the object,
the calculation unit calculates the degree of matching for each of the two or more types of feature parts, and
the display control unit combines the degrees of matching of the two or more types of feature parts calculated by the calculation unit and causes the display unit to display the combination.

8. The image processing apparatus according to claim 7, wherein the object is a breast, and the obtainment unit obtains at least a nipple of the breast and a point on a body surface of the breast as the feature parts of the object.

9. The image processing apparatus according to claim 8, wherein the calculation unit calculates the degree of matching based on, in the first image, a distance between the point on the body surface of the breast which is a nearest neighbor in relation to the position of the first point and the nipple of the breast, and in the second image, a distance between a point on the body surface of a breast which is a nearest neighbor in relation to the position of the second point and the nipple of the breast.

10. The image processing apparatus according to claim 1, wherein the second image is real space.

11. The image processing apparatus according to claim 1, wherein
the specification unit is configured to specify a plurality of second points on the second image;
the calculation unit is configured to, based on the positional relationship between the first point on the first image and the feature part of the object on the first image, and a positional relationship between each of the plurality of second point on the second image and the feature part of the object on the second image, calculate a distribution of the degree of matching between the first point and the plurality of second point;
the display control unit is configured to cause the display unit to display the distribution of the calculated degree of matching.

12. The image processing apparatus according to claim 1, wherein the display control unit causes the display unit to display the calculated degree of matching as a numerical value.

13. The image processing apparatus according to claim 1, wherein the display control unit causes the display unit to display the calculated degree of matching using at least one of character information, symbol information, and an indicator.

14. The image processing apparatus according to claim 1, wherein the calculation unit continues to recalculate the degree of matching while updating a position of the second point.

15. The image processing apparatus according to claim 1, wherein the specification unit is a cursor operable with a mouse or a keyboard.

16. The image processing apparatus according to claim 1, wherein the display control unit causes the display unit to display the calculated degree of matching together with the second image.

17. The image processing apparatus according to claim 1, wherein the display control unit causes the display unit to display the calculated degree of matching together with the second point based on the changed position on the second image.

18. The image processing apparatus according to claim 1, wherein the one or more processors which, by executing the program, further function as:
a registration execution unit configured to execute a registration between the first image and the second image using information of a corresponding point group which includes the second point based on the changed position on the second image.

19. A method of controlling an image processing apparatus, the method comprising:
obtaining, in a first image and a second image obtained by capturing an object, a feature part of the object;
specifying a first point on the first image and a second point on the second image;
based on a positional relationship between the first point on the first image and the feature part of the object on the first image, and a positional relationship between the second point on the second image and the feature part of the object on the second image, calculating a degree of matching between the first point and the second point;
causing a display unit to display the calculated degree of matching; and
in a case where a position of the second point on the second image is changed, recalculating, based on the positional relationship between the first point on the first image and the feature part of the object on the first image, and the positional relationship between the second point based on the changed position on the second image and the feature part of the object on the second image, the degree of matching between the first point on the first image and the second point based on the changed position on the second image.

20. The method of controlling the image processing apparatus according to claim 19, wherein the first image and the second image are obtained by capturing the object under different conditions.

21. The method of controlling the image processing apparatus according to claim 19, the degree of matching is calculated based on a first distance from the first point on the first image to a position of the feature part of the object on the first image and a second distance from the second point on the second image to a position of the feature part of the object on the second image.

22. The method of controlling the image processing apparatus according to claim 19, wherein the object is a breast, and
a nipple of the breast or a point on a body surface of a breast is obtained as the feature part of the object.

23. The method of controlling the image processing apparatus according to claim 19, wherein two or more types of feature parts of the object are obtained,
the degree of matching is calculated for each of the two or more types of feature parts, and
the calculated degrees of matching of the two or more types of feature parts are combined and the display unit is caused to display the combination.

24. The method of controlling the image processing apparatus according to claim 23, wherein the object is a breast, and
at least a nipple of the breast and a point on a body surface of a breast is obtained as the feature parts of the object.

25. The method of controlling the image processing apparatus according to claim 19, wherein the second image is real space.

26. The method of controlling the image processing apparatus according to claim 19, wherein,
a plurality of second points on the second image is specified;
based on the positional relationship between the first point on the first image and the feature part of the object on the first image, and a positional relationship between each of the plurality of second point on the second image and the feature part of the object on the second image, a distribution of the degree of matching between the first point and the plurality of second point is calculated;
the distribution of the calculated degree of matching is displayed.

27. A non-transitory computer-readable storage medium storing a computer program for causing a computer to execute a control method of an image processing apparatus, the method comprising:
obtaining, in a first image and a second image obtained by capturing an object, a feature part of the object;
specifying a first point on the first image and a second point on the second image;
based on a positional relationship between the first point on the first image and the feature part of the object on the first image, and a positional relationship between the second point on the second image and the feature part of the object on the second image, calculating a degree of matching between the first point and the second point;
causing a display unit to display the calculated degree of matching; and
in a case where a position of the second point on the second image is changed, recalculating, based on the positional relationship between the first point on the first image and the feature part of the object on the first image, and the positional relationship between the second point based on the changed position on the second image and the feature part of the object on the second image, the degree of matching between the first point on the first image and the second point based on the changed position on the second image.

28. An image processing apparatus, comprising:
a memory storing a program; and
one or more processors which, by executing the program, function as:
an obtainment unit configured to obtain, in a first image and a second image obtained by capturing an object, a feature part of the object;
a deformation unit configured to deform the first image and the second image to a first deformation image and a second deformation image, respectively;
a coordinate transformation unit configured to calculate a position of a second point on the first image corresponding to a position of a first point on the first deformation image, and a position of a fourth point of the second image corresponding to a position of a third point of the second deformation image;
a calculation unit configured to calculate, based on a positional relationship between the second point and the feature part of the object on the first image and a positional relationship between the fourth point and the feature part of the object on the second image, a degree of matching between the second point and the fourth point; and a display control unit configured to cause a display unit to display the calculated degree of matching.

29. A method of controlling an image processing apparatus, the method comprising:
obtaining, in a first image and a second image obtained by capturing an object, a feature part of the object;
deforming the first image and the second image to a first deformation image and a second deformation image, respectively;
calculating a position of a second point on the first image corresponding to a position of a first point on the first deformation image, and a position of a fourth point of the second image corresponding to a position of a third point of the second deformation image;
calculating, based on a positional relationship between the second point and the feature part of the object on the first image and a positional relationship between the fourth point and the feature part of the object on the second image, a degree of matching between the second point and the fourth point; and
causing a display unit to display the calculated degree of matching.

30. A non-transitory computer-readable storage medium storing a computer program for causing a computer to execute a control method of an image processing apparatus, the method comprising:
obtaining, in a first image and a second image obtained by capturing an object, a feature part of the object;
deforming the first image and the second image to a first deformation image and a second deformation image, respectively;
calculating a position of a second point on the first image corresponding to a position of a first point on the first deformation image, and a position of a fourth point of the second image corresponding to a position of a third point of the second deformation image;
calculating, based on a positional relationship between the second point and the feature part of the object on the first image and a positional relationship between the fourth point and the feature part of the object on the second image, a degree of matching between the second point and the fourth point; and
causing a display unit to display the calculated degree of matching.

* * * * *